(12) United States Patent
Jones et al.

(10) Patent No.: US 11,014,962 B2
(45) Date of Patent: May 25, 2021

(54) METHOD FOR PROTEIN PURIFICATION (71) Applicant: UCB BIOPHARMA SRL, Brussels (BE)

(72) Inventors: Richard Jones, Slough (GB); Jonathan Symmons, Slough (GB); Saskia Hocking, Slough (GB)

(73) Assignee: UCB BIOPHARMA SRL, Brussels (BE)

(*) Notice: Subject to any disclaimer, the term of this patent is extended or adjusted under 35 U.S.C. 154(b) by 167 days.

(21) Appl. No.: 16/089,443

(22) PCT Filed: Mar. 31, 2017

(86) PCT No.: PCT/EP2017/057685
§ 371 (c)(1),
(2) Date: Sep. 28, 2018

(87) PCT Pub. No.: WO2017/167960
PCT Pub. Date: Oct. 5, 2017

(65) Prior Publication Data
US 2019/0153028 A1   May 23, 2019

(30) Foreign Application Priority Data

Apr. 1, 2016 (GB) .................................. 1605562

(51) Int. Cl.

| | | |
|---|---|---|
| *C07K 16/00* | (2006.01) | |
| *C07K 1/16* | (2006.01) | |
| *C07K 1/36* | (2006.01) | |
| *A23J 1/00* | (2006.01) | |
| *B01D 15/18* | (2006.01) | |
| *C07K 1/22* | (2006.01) | |
| *B01D 15/26* | (2006.01) | |
| *B01D 15/38* | (2006.01) | |
| *C07K 1/20* | (2006.01) | |
| *B01J 20/20* | (2006.01) | |
| *B01J 47/014* | (2017.01) | |
| *B01D 15/36* | (2006.01) | |
| *B01J 20/282* | (2006.01) | |
| *C07K 1/18* | (2006.01) | |
| *C07K 1/34* | (2006.01) | |

(52) U.S. Cl.
CPC ............ *C07K 1/22* (2013.01); *B01D 15/1871* (2013.01); *B01D 15/265* (2013.01); *B01D 15/362* (2013.01); *B01D 15/363* (2013.01); *B01D 15/3809* (2013.01); *B01J 20/20* (2013.01); *B01J 20/282* (2013.01); *B01J 47/014* (2017.01); *C07K 1/18* (2013.01); *C07K 1/20* (2013.01); *C07K 1/34* (2013.01); *C07K 16/00* (2013.01)

(58) Field of Classification Search
CPC ................ B01D 15/362; B01D 15/363; B01D 15/3809; A61P 35/00; A61P 3/04
See application file for complete search history.

(56) References Cited

U.S. PATENT DOCUMENTS

2014/0046038 A1    2/2014  Ishihara

FOREIGN PATENT DOCUMENTS

| CN | 104546715 | 4/2015 |
|---|---|---|
| EP | 2 682 168 | 1/2014 |
| JP | S56-59795 | 5/1981 |
| WO | WO 2010/141039 | 12/2010 |
| WO | WO 2013/028330 | 2/2013 |
| WO | WO 2013/148389 | 10/2013 |
| WO | WO 2015/005960 | 1/2015 |
| WO | WO 2015/005961 | 1/2015 |
| WO | WO2015005960 | * 1/2015 |

OTHER PUBLICATIONS

Xenopoulos, A. E. et al. "A new, integrated, continuous purification process template for monoclonal antibodies: Process modeling and cost of goods studies" *Journal of Biotechnology* Jan. 1, 2015, pp. 42-53, vol. 213.

Written Opinion in International Application No. PCT/EP2017/057685, dated May 15, 2017, pp. 1-5.

Kao, Y.-H. et al. "Mechanism of Antibody Reduction in Cell Culture Production Processes" *Biotechnol. Bioeng.*, 2010, pp. 622-632, vol. 107, No. 4.

* cited by examiner

*Primary Examiner* — Barry A Chestnut
(74) *Attorney, Agent, or Firm* — Saliwanchik, Lloyd & Eisenschenk (57) ABSTRACT

The present invention provides a method for manufacturing antibodies or a fragment thereof with reduced levels of antibody reduction related impurities.

15 Claims, 8 Drawing Sheets

METHOD FOR PROTEIN PURIFICATION

CROSS-REFERENCE TO RELATED APPLICATION

This application is the U.S. national stage application of International Patent Application No. PCT/EP2017/057685, filed Mar. 31, 2017.

BACKGROUND OF THE INVENTION

In the field of therapeutics the use of proteins, and antibodies and antibody-derived molecules in particular has been constantly gaining presence and importance, and, consequently, the need for controlled manufacturing processes has developed in parallel. The commercialization of therapeutic proteins requires they be produced in large amounts. For this purpose the protein is frequently expressed in a host cell and must subsequently be recovered and purified, prior to its preparation into an administrable form. Impurities that are removed during said purification are typically classified as process related impurities including host cell debris, host cell proteins, traces of culture media, etc. and product-related impurities resulting from the modification, degradation or aggregation of the desired product.

The most common class of antibody molecule is immunoglobulin G (IgG), a heterotetramer composed of two heavy chains and two light chains. The IgG molecule can be subdivided into two functional subunits: (1) the fragment crystallizable (Fc), which constitutes the tail of the antibody and interacts with cell surface receptors to activate an immune response, and (2) the fragment antigen-binding (Fab), which mediates antigen recognition. The Fc region comprises two pairs of constant domains (CH2 and CH3) from two paired heavy chains, whereas the Fab region consists of a variable domain followed by a constant domain from the heavy chain (VH and CH1, respectively), which pair with a variable and constant domain from the light chain (VL and CL, respectively). The Fc and Fab regions are demarcated by a hinge region, which contains a disulfide linkage holding the two heavy chains together; further disulfide bridges within the CH1 and CL domains pair the heavy and light chains together.

Full-length antibodies of the IgG class have traditionally been purified using methods that include a capture step of affinity chromatography using protein A derived from *Staphylococcus aureus*. The high-specificity of binding between Protein A and the Fc-region of antibodies enables this mode of chromatography to remove more than 98% of the impurities in a single step starting directly from complex solutions such as cell culture harvest media. The large purification factor obtained from this process step helps to simplify the entire downstream purification process. In general, only trace impurities such as high molecular weight aggregates, residual host cell proteins, Residual DNA, or leached protein A, remain to be removed after this purification step and this can usually be achieved in one to two subsequent chromatographic steps.

Despite the fact that protein A-based antibody purification has been used and developed over the past decades, the manufacture of recombinant antibodies on an industrial scale with a level of purity that is suitable for administration remains a challenge. In particular proteins such as antibodies and fragments thereof comprise inter-chain disulfide bonds that typically need protecting and maintaining during the manufacturing and purification process, in order to produce antibodies in their native conformation thus retaining their biological activity.

Where these inter-chain disulfide bonds are affected by the environment and become reduced, the different polypeptide chains will separate resulting in a type of impurity consisting of incomplete antibody molecules that must be removed from the final antibody preparation. As the environment becomes oxidizing later during the purification process, these reduction related impurities may reform incorrectly resulting in increased levels of product related high and low molecular weight species. The purification of the additional impurities generated results in decreased process yields and increased impurity levels in the final drug substance. Furthermore, reproducibility across manufacturing batches must be ensured and therefore controlling the presence and relative amount of such impurities is essential to avoid the failure of specific manufacturing batches. Batch failure may be due to either increased impurity levels in the drug substance, or failure to meet an in-process control. The increased level of impurities in the drug substance may also decrease the shelf life of the drug product.

Figure 1:
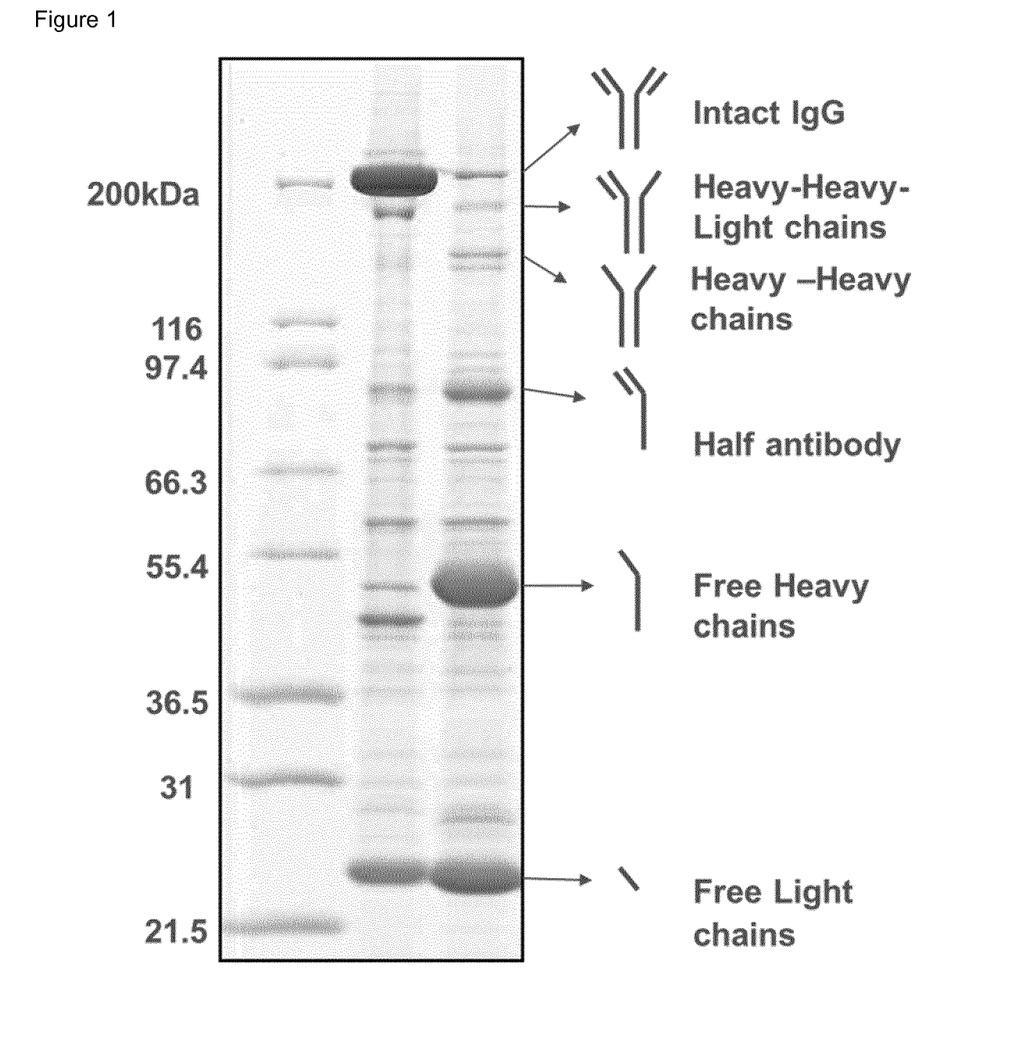
FIG. 1: Coomassie stained non-reducing gel electrophoresis showing possible product-related impurities recovered from a sample of antibody after undergoing purification.

During antibody manufacture the appearance of product-related impurities such as free heavy and light chains, halfmers (one heavy chain and one light chain) or isoforms partly lacking disulfide bonds, due to reduction of interchain disulfide bonds has been observed after the protein A chromatography step. Appearance of these impurities during the purification process must be avoided and the impurities removed as part of said process. Possible product related impurities can be analyzed by non-reducing Sodium Dodecyl Sulphate Polyacrylamide Gel Electrophoresis (SDS PAGE) and are shown in FIG. 1.

In this sense, U.S. Pat. No. 8,574,869 discloses a method for preventing disulfide bond reduction during harvesting of recombinant proteins from host cell cultures.

There remains therefore a need in the art for reproducible methods of protein manufacture that allow purification of the proteins in their native conformation with a consistent degree of purity across different batches.

DETAILED DESCRIPTION OF THE INVENTION

The present invention solves the above identified need by providing a new method for antibody manufacture that allows for recovery of the antibody with native disulfide bonds, thus improving process yield and ensuring consistency across batches.

Therefore in a first aspect, the invention provides a method for manufacturing an antibody or fragment thereof comprising:
 expressing said antibody or fragment thereof in a host cell;
 recovering a mixture containing the antibody or fragment thereof, host cell debris, and impurities; and
 purifying said antibody or fragment thereof from the mixture wherein said purification comprises:
 activated carbon filtration, followed by
 protein A chromatography.

In a second aspect the invention provides a method for the prevention of disulfide bond reduction during purification of an antibody or fragment thereof expressed in a host cell comprising:
 activated carbon filtration, followed by
 protein A chromatography.

In a third aspect the invention provides a method for purifying an antibody or fragment thereof comprising:
 activated carbon filtration, followed by
 protein A chromatography.

In a fourth aspect the invention provides a method for decreasing the amount of reducing agents during purification of an antibody or antibody fragment thereof comprising:
 activated carbon filtration, followed by
 protein A chromatography.

A reducing agent, also referred to in the art as a reductant or a reducer is an element or compound that loses (or donates) an electron to another chemical species in a redox chemical reaction. Since the reducing agent is losing electrons it is considered to have been oxidized. Certain reducing agents such as for example calcium can be present in the cell culture media, further reducing agents can be secreted to the cell culture fluid as a consequence of host cell metabolism. Also, during recombinant protein manufacture reducing agents can be further liberated in the medium due to shear forces and consequent cellular damage and possible lysis and/or apoptosis releasing cellular components into the environment. The amount and power of the reducing agents of the released cell contents is cell line and process dependent; examples of such reducing agents include but are not limited to glutathione, cysteinyl glycinate, cysteinyl sulphonate, thioredoxin, NADP, NADPH, NAD, NADH.

In a particular embodiment of the fourth aspect of the invention, the method of the invention reduces the amount of thioredoxin, NADP, NADPH, NAD, and/or NADH.

In a further particular embodiment of the fourth aspect of the invention, the method of the invention reduces the amount of thioredoxin, NADP, NADPH, NAD, and/or NADH.

Typically, protein A chromatography is performed in bind and elute mode, wherein binding of the protein of interest to the solid phase allows the impurities such as host cell proteins to flow through the chromatographic medium while the protein of interest remains bound to the solid phase. The bound protein of interest is then recovered from the solid phase with an elution buffer that disrupts the mechanism by which the protein of interest is bound to said solid phase.

In a further embodiment of the method of the invention a first solution is added to the protein A chromatography material after applying the mixture comprising the antibody or fragment thereof, such that unbound material is removed in the solution.

In a further embodiment of the method according to the invention an elution buffer is applied to the protein A chromatography material such that the bound antibody or fragment thereof is released.

In a particular embodiment of the method of the invention the bound antibody is released from the protein A chromatography material by applying an elution buffer with a pH suitable to disrupt antibody binding. Said pH is dependent on the specific molecule and generally determined empirically by the skilled artisan and adjusted to achieve the desired endpoint, i.e. it may be desired to recover the largest amount of monomer possible from the applied mixture, or it may be desirable to obtain the monomer at the highest possible purity. In a specific embodiment of the method of the invention the elution buffer has pH 3 to pH 4.5, preferably, pH 3.2 to pH 4.3, pH 3.5 to pH 4, preferably pH 3.6 to pH 3.9.

Buffers suitable for use as wash and elution buffers in protein A chromatography are readily available in the art, and may be chosen by way of non-limiting examples from among phosphate buffered saline (PBS), Tris, histidine, acetate, citrate buffers, or MES (2-(N-morpholino)ethanesulphonic acid Imidazole), BES (N,N-(bis-2-hydroxyethyl)-2-aminoethanesulphonic acid), MOPS (3-(N-morpholino)-propanesulphonic acid), or HEPES (N-2-hydroxyethylpiperazine-N'-2-ethanesulphonic acid) buffers.

In a second embodiment the invention provides a method according to the first, second, third or fourth aspect wherein said purification comprises at least one further chromatography step. Said further additional chromatography steps are selected from anion or cation exchange chromatography, hydrophobic interaction chromatography, mixed-mode chromatography, such as hydroxyapatite chromatography, chiral chromatography or dielectric chromatography. These chromatography steps may be used in isolation or alternatively, in combination with yet another chromatography step. Furthermore, these chromatography steps may be operated in bind and elute mode or in flow-through mode. In flow-through mode, the impurities bind or have reduced mobility in the solid phase whereas the target protein is recovered in the eluate or flow through fraction. In a further particular embodiment, said further chromatography steps are performed after the Protein A chromatography.

In a third embodiment the invention provides a method according to the second embodiment, wherein said further chromatography steps comprise cation exchange chromatography and/or anion exchange chromatography.

In a particular embodiment of the invention said first further chromatography step is an anion exchange chromatography step to capture impurities and produce a flow-through containing the protein.

In another particular embodiment of the invention, the first further chromatography step is followed by a cation exchange chromatography step wherein the protein of interest binds to the chromatographic medium and is subsequently eluted into an eluate containing the protein. Alternatively said cation exchange chromatography step is operated in such a way to capture impurities and produce a flow-through containing the protein.

In a further embodiment the invention provides a method according to the second or third embodiment wherein said further chromatography steps comprise a first step of anion exchange chromatography and a second step of cation exchange chromatography.

In an alternative embodiment the invention provides a method according to the second or third embodiment wherein said further chromatography steps comprise a first step of cation exchange chromatography and a second step of anion exchange chromatography.

In further embodiments one or more ultrafiltration or diafiltration (UF/DF) steps are performed between the chromatography steps. In industrial-scale protein manufacture, this is typically operated using a membrane based tangential flow filtration step performed for the purpose of product concentration and buffer exchange. These membranes are usually low protein binding and have a specific nominal molecular weight cutoff to prevent product loss, for example these include polyethersulfone (PES) membranes with a 30 kDa nominal molecular weight cutoff (T-series Omega PES membrane from Pall Life Sciences) or regenerated cellulose with a 30 kDa nominal molecular weight cutoff (Delta Regenerated Cellulose Membrane from Pall Life Sciences). Alternatively, membranes with a 30 kDa molecular weight cutoff are used such as Pellicon 3 from Millipore or Hydrosart from Sartorius.

A purification strategy can include any of these steps in various combinations to suit the physical-chemical properties of the target protein.

In a further particular embodiment of the method of the invention, the step of protein purification from a mixture comprises a first further chromatography step that is an anion exchange chromatography from where a first flow-through containing the protein is recovered, a second further chromatography step that is a cation exchange chromatography from which an eluate containing the protein is eluted; and a second ultrafiltration or diafiltration step applied to the eluate.

In a further particular embodiment of the method of the invention, the step of protein purification from a mixture comprises a first further chromatography step that is a cation exchange chromatography from where a first eluate containing the protein is eluted, a first ultrafiltration or diafiltration step applied to the first eluate, a second further chromatography step that is an anion exchange chromatography to produce a flow-through containing the protein; and a second ultrafiltration or diafiltration step applied to the flow-through.

In a further particular embodiment of the method of the invention, the purification process further comprises an ultrafiltration or diafiltration step after the protein A chromatography and before the further chromatography steps.

In a fourth embodiment the invention provides a method according to any of the preceding embodiments, wherein the recovered antibody or fragment thereof comprises native disulfide bonds.

In a fifth embodiment the invention provides a method according to any of the preceding embodiments wherein the recovered antibody or fragment thereof comprises native inter-chain disulfide bonds.

In a further embodiment according to any of the aspects of the invention, the invention provides a method according to any of the preceding embodiments wherein the antibody or fragment recovered from the protein A chromatography comprises less than 10%, less than 5%, less than 4%, less than 3%, less than 2% or less than 1% antibody reduction related impurities.

In another further embodiment according to any of the aspects of the invention, the invention provides a method according to any preceding embodiments wherein the antibody or fragment thereof recovered from the protein A chromatography comprises less antibody reduction related impurities than the antibody or fragment recovered from the same process without an activated carbon filtration step.

In a further alternative embodiment according to any of the aspects of the invention, the invention provides a method according to any preceding embodiment wherein the purified antibody or fragment thereof has a reduced level of antibody reduction related impurities.

In a further alternative embodiment according to any of the aspects of the invention, the invention provides a method according to any preceding embodiments wherein the purified antibody or fragment thereof has a reduced level of antibody reduction related impurities after the protein A chromatography step.

In a sixth embodiment the invention provides a method according to any of the preceding embodiments wherein said host cell is a mammalian host cell and the mixture containing the antibody is the cell culture supernatant.

In a seventh embodiment the invention provides a method according to the fifth embodiment wherein said purification process additionally comprises depth filtration of the cell culture supernatant prior to activated carbon filtration.

In a further possible embodiment of the invention said filtration sequence may comprise additional filters available to the skilled artisan such as for example a sterilizing filter.

Successive filtration steps during protein purification may be performed as separate steps, wherein the mixture to be filtered is passed through one filter, the filtrate recovered and then passed through a second filter from which a second filtrate is recovered. Alternatively, said filtration steps may be operated in-line, where one filter is adjacent to the next so the media to be filtered is passed successively through both filters and one filtrate is recovered after this step; said in-line set up is commonly referred to as a filter train.

In an eighth embodiment the invention provides a method according to the seventh embodiment wherein depth filtration and activated carbon filtration are operated in-line.

Alternatively, in another particular embodiment of the seventh embodiment of the method of the invention, depth filtration and activated carbon filtration are separate steps.

Host cells according to the embodiments of the invention are for example prokaryotic, yeast (for example without limitation *Candida boidinii, Hansenula polymorpha, Pichia methanolica, Pichia pastoris, Saccharomyces cerevisiae,*

Schizosaccharomyces pombe, Kluyveromyces lactis and other Kluyveromyces spp., Yarrowia lipolytica), Myxomycete (for example without limitation Dictyostelium discoideum), filamentous fungi (for example without limitation Trichoderma reesei and other Trichoderma spp., Aspergillus niger and other Aspergillus spp.), moss (for example without limitation Physcomitrella patens, Atrichum undulatum), insect or mammalian cells. Mammalian host cells are, for example without limitation of NSO, SP2.0, 3T3 cells, COS cells, human osteosarcoma cells, MRC-5 cells, baby hamster kidney (BHK) cells, VERO cells, CHO cells, rCHO-tPA cells, rCHO-Hep B Surface Antigen cells, CHO-S cells, HEK 293 cells, rHEK 293 cells, C127 cells, rC127-Hep B Surface Antigen cells, human fibroblast cells, Stroma cells, hepatocyte cells or PER.C6 cells.

The host cells are preferably eukaryotic host cells, preferably mammalian host cells, more preferably Chinese Hamster Ovary (CHO) cells, e.g. of the DG44 strain.

For eukaryotic host cells (e.g. yeasts, insect or mammalian cells), different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA, can be selected by also introducing one or more markers, which allow for selection of host cells, which contain the expression vector. The marker may also provide for phototrophy to an auxotropic host, biocide resistance, for example without limitation antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

The eukaryotic host cells are transfected with one or more expression vectors encoding the protein of interest and subsequently cultured in any medium that will support their growth and expression of the protein of interest. The medium is a chemically defined medium that is free of animal derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 400 L, 1,000 L to 50,000 L or 100,000 L, preferably between 5,000 L and 20,000 L, or to 10,000 L. Alternatively, bioreactors of a smaller scale such as between 2 L, 80 L and 100 L may also be used to manufacture an antibody according to the method of the invention.

A protein of interest, such as an antibody or antigen-binding fragment that is produced in a eukaryotic host cell, such as a CHO cell, in accordance with the process and methods of the present invention is typically found in the supernatant of the cell culture. In an embodiment of the invention said supernatant is the mixture purified in the process of the invention.

Therefore in a particular embodiment of the invention, the process and methods of the invention comprises a step of centrifugation of the cell culture fluid and recovery of the liquid phase following centrifugation in order to obtain the mixture containing the antibody or fragment thereof for further purification according to the process of the invention.

Alternatively or additionally said supernatant may be recovered using clarification techniques known to the skilled artisan such as for example depth filtration. Therefore in a particular embodiment of the invention, the method comprises a step of depth filtration in order to obtain the mixture containing the antibody or fragment thereof for further purification according to the process of the invention.

Alternatively, host cells are prokaryotic cells, preferably gram-negative bacteria, preferably, E. coli cells. Prokaryotic host cells for protein expression are well known in the art (Terpe, 2006; Appl Microbiol Biotechnol 72, 211-222.). The host cells are recombinant cells which have been genetically engineered to produce the protein of interest such as an antibody fragment. The recombinant E. coli host cells may be derived from any suitable E. coli strain including from MC4100, TG1, TG2, DHB4, DH5α, DH1, BL21, K12, XL1Blue and JM109. One example is E. coli strain W3110 (ATCC 27,325) a commonly used host strain for recombinant protein fermentations. Antibody fragments can also be produced by culturing modified E. coli strains, for example metabolic mutants or protease deficient E. coli strains.

An antibody fragment that can be purified in accordance with the methods of the present invention is typically found in either the periplasm of the E. coli host cell or in the host cell culture supernatant, depending on the nature of the protein, the scale of production and the E. coli strain used. The methods for targeting proteins to these compartments are well known in the art (Makrides, 1996; Microbiol Rev 60, 512-538). Examples of suitable signal sequences to direct proteins to the periplasm of E. coli include the E. coli PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host E. coli.

Expression of the recombinant protein in the E. coli host cells may also be under the control of an inducible system, whereby the expression of the recombinant antibody in E. coli is under the control of an inducible promoter. Many inducible promoters suitable for use in E. coli are well known in the art and depending on the promoter; expression of the recombinant protein can be induced by varying factors such as temperature or the concentration of a particular substance in the growth medium. Examples of inducible promoters include the E. coli lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

E. coli host cell cultures (fermentations) may be cultured in any medium that will support the growth of E. coli and expression of the recombinant protein. The medium may be any chemically defined medium such as e.g. described in (Durany O, 2004; Process Biochem 39, 1677-1684).

Culturing of the E. coli host cells can take place in any suitable container such as a shake flask or a fermenter depending on the scale of production required. Various large scale fermenters are available with a capacity of more than 1,000 L up to 100,000 L. Preferably, fermenters of between 1,000 L and 50,000 liters are used, more preferably of between 1,000 L and 10,000 L or 12,000 L. Smaller scale fermenters may also be used with a capacity of between 0.5 L and 1,000 L.

Fermentation of host cells such as, CHO or E. coli, may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete.

In one embodiment the process according to the present invention comprises prior to the loading onto the protein A chromatography matrix a step of centrifugation of cell culture harvest, followed by suspension of the host cells by addition of the extraction buffer.

For E. coli fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art.

The term "activated carbon" as used herein refers to a form of carbon that has been processed to create millions of tiny pores between the carbon atoms, resulting in a dramatically increased surface area. The surface area of activated carbon makes the material suitable for adsorption, a process by which impurities are removed from fluids, vapors or gas. Activated carbon is also known as activated charcoal. Commercially available activated carbon filters include but are not limited to Millipore Millistak+ CR series, Pall Activated Carbon Filters Incorporating Seitz® AKS Filter Media, and 3M Zeta Plus™ Activated Carbon Filters.

The term "anion exchange chromatography" as used herein refers to a chromatography wherein the solid phase is positively charged, e.g. having one or more positively charged ligands, such as quaternary amino groups, attached thereto. Commercially available anion exchange matrices include DEAE cellulose, QAE SEPHADEX™, FAST Q SEPHAROSE™ Capto Q, Capto Adhere and Capto Q Impres (GE Healthcare), Unosphere and Nuvia Q (BioRad), GigaCap Q (Tosoh), Mustang Q XT (Pall), Fractogel Q and Eshmuno Q (Merck Millipore), Poros XQ (Thermo Fisher) and anion exchange membrane adsorbers such as SartoBind Q (Sartorius), and monolith adsorbers such as QA monoliths (Bia Separations).

The term "antibody" or "antibodies" as used herein, refers to monoclonal or polyclonal tetrameric full length antibodies comprising two heavy and two lights chains. The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit, hamster or guinea pig), goat, bovine or horse species. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine. Preferred molecular targets for antibodies encompassed by the present invention include CD polypeptides such as CD3, CD4, CD8, CD19, CD20, CD22, CD34, CD38, CD40 and CD40-L; FcRN; OX40; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either α or β subunits thereof (e.g. anti-CD11a, anti-CD18 or anti-CD11b antibodies); chemokines and cytokines or their receptors such as IL-1 α and β, IL-2, IL-6, the IL-6 receptor, IL-12, IL-13, IL-17A and/or IL-17F, IL-18, IL-21, IL-23, TNFα and TNFβ; growth factors such as VEGF; IgE; blood group antigens; flk2/flt3 receptor; obesity (OB) receptor; mpl receptor; CTLA-4; polypeptide C; PD1, PD-L1, PCSK9; sclerostin; etc.

The term "antibody fragment" or "antibody fragments" as used herein, refers a portion of an antibody, generally the antigen binding or variable region thereof. Examples of antibody fragments include any antibody that lacks the or has no Fc portion. Examples of antibody fragments include also such as Fab, Fab', F(ab')2, and Fv and scFv fragments; as well as diabodies, including formats such as BiTEs® (Bi-specific T-cell Engagers) and DARTs™ (Dual Affinity Re-Targeting technology), triabodies, tetrabodies, minibodies, domain antibodies (dAbs), such as sdAbs, VHH and VNAR fragments, single-chain antibodies, bispecific, trispecific, tetraspecific or multispecific antibodies formed from antibody fragments or antibodies, including but not limited to Fab-Fv, Fab-scFv, Fab(Fv)$_2$ or Fab-(scFv)$_2$ constructs. Antibody fragments as defined above are known in the art. For the purpose of clarity Fab-Fv should be understood to refer to a construct containing one Fv region and one Fab region joined in any order, i.e. Fab-Fv, or Fv-Fab, wherein the last amino acids in one region are followed by the first amino acids in the next region or vice versa. Similarly Fab-scFv should be understood to refer to a construct containing one scFv region and one Fab region joined in any order and in the case of the Fab to either polypeptide chain, i.e. Fab-scFv, or scFv-Fab, wherein the last amino acid in one region is followed by the first amino acid in the next region or vice versa. In the same manner Fab-(Fv)2 should be understood to refer to a construct containing two Fv regions and one Fab region joined in any order, i.e. Fab-Fv-Fv, Fv-Fab-Fv, or Fv-Fv-Fab, wherein the last amino acids in one region are followed by the first amino acids in the next region or vice versa. Similarly Fab-(scFv)2 should be understood to refer to a construct containing two scFv regions and one Fab region joined in any order and in the case of the Fab to either polypeptide chain, resulting in 20 possible permutations. Typically these constructs include a peptide linker between the first region (e.g. Fab) and the second region (e.g. Fv). Such linkers are well known in the art, and can be one or more amino acids, typically optimized in length and composition by a skilled artisan. Alternatively said regions may be linked directly, i.e. without a peptide linker. Examples of suitable linker regions for linking a variable domain to a Fab or Fab' are described in WO 2013/068571 incorporated herein by reference, and include, but are not limited to, flexible linker sequences and rigid linker sequences. Flexible linker sequences include those disclosed in Huston et al., 1988, 10 PNAS 85:5879-5883; Wright & Deonarain, Mol. Immunol., 2007, 44(11):2860-2869; Alfthan et al., Prot. Eng., 1995, 8(7):725-731; Luo et al., J. Biochem., 1995, 118(4):825-831; Tang et al., 1996, J. Biol. Chern. 271(26): 15682-15686; and Turner et al., 1997, JIMM 205, 42-54. Antibody fragments can be aglycosylated or glycosylated.

The term "antibody reduction related impurities" as used herein refers impurities such as free heavy and light chains, halfmers (one heavy chain and one light chain) or isoforms partly lacking disulfide bonds, that appear due to reduction of interchain disulfide bonds.

The term "cation exchange chromatography" as used herein refers to a chromatography wherein the solid phase which is negatively charged, e.g. having one or more negatively charged ligands, such as for example a carboxylate or sulphonate group. Commercially available cation exchange matrices include carboxy-methyl-cellulose, sulphopropyl (SP) immobilized on agarose and sulphonyl immobilized on agarose such as Capto S, and Capto S Impres (GE Healthcare), Unosphere S and Nuvia S (BioRad), GigaCap S (Tosoh), Fractogel S and Eshmuno S (Merck Millipore) Poros S and Poros XS (Thermo Fisher) or cation exchange membrane adsorbers such as SartoBind S (Sartorius) and monolith adsorbers such as SO3 monoliths (Bia Separations).

The term "Protein A" as used herein encompasses Protein A recovered from a native source thereof, Protein A produced synthetically (e.g. by peptide synthesis or by recombinant techniques), and variants thereof which retain the ability to bind proteins which have a CH2/CH3 region, such as an Fc region. Protein A can be purchased commercially from Repligen, GE Healthcare, and Fermatech. Protein A is generally immobilized on a solid phase support material, such as a membrane or resin. The term "Protein A" also refers to an affinity chromatography resin or column containing chromatographic solid support matrix to which Protein A is covalently attached. Commercially available Protein A matrices include MabSelect, MabSelect SuRe, MabSelect SuRe LX from GE Healthcare; Amsphere Protein A (JSR Life Sciences), KanCapA (Kaneka), AbSolute® High Cap (NovaSep), UNOsphere SUPrA (BioRad), Toyopearl (Toso BioScience), Prosep Ultra plus, Eshmuno A, ProSep®-vA, ProSep®-vA Ultra from Millipore, Poros Mab-Capture A (Life Technologies), and Praesto AC (Purolite).

The term "depth filter" as used herein refers to a variety of filters that use a porous filtration medium to retain particles throughout the medium, rather than just on the surface of the medium. They are typically used for fluids that contain a high load of particles as they can retain a larger mass of particles before becoming saturated.

EXAMPLES

Figure 3:
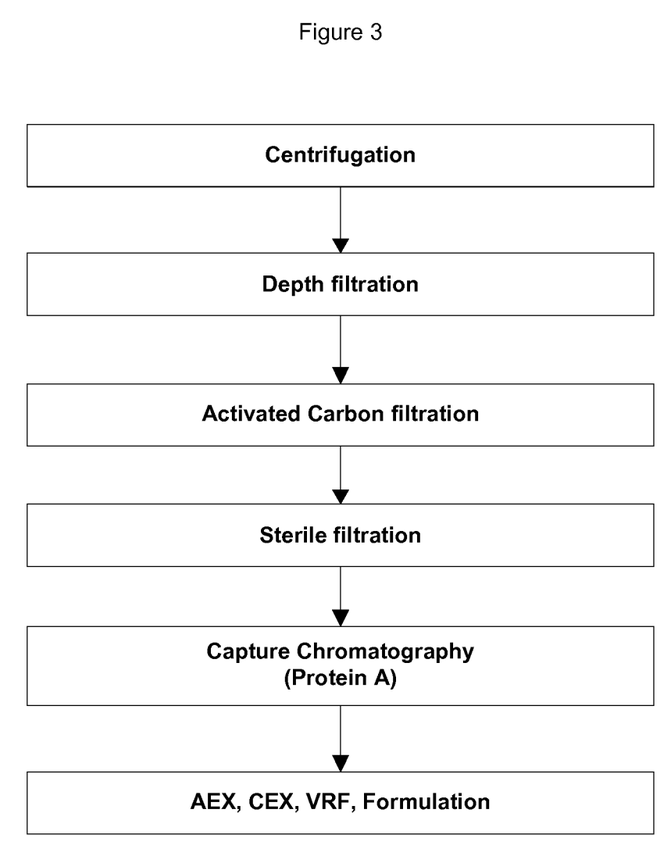
FIG. 3: Purification process flow diagram including carbon filtration. The activated carbon filter step was implemented inline between depth filtration and the sterile filter. It was followed by the capture step using Protein A, and the subsequent purification steps: anion exchange chromatography (AEX), cation exchange chromatography (CEX), viral reduction filtration (VRF), and formulation.

Example 1: Prevention of Antibody Reduction in a 2000 L Bioreactor Scale Process In the present example the manufacture of Molecule A at 2000 L scale exhibited significant antibody reduction in campaign 2 after the protein A capture chromatography step. In the subsequent manufacturing campaign (campaign 3) an activated carbon filtration step was implemented (Millistak+ CR40, Millipore) in the primary recovery process as depicted in FIG. 3. No antibody reduction was detected in this campaign.

Molecule A is a humanized monoclonal IgG4P antibody expressed in a CHO DG44 cell line in a fed batch bioreactor process and purified with a 3 step chromatography process. The theoretical intact mass for the complete glycosylated molecule was determined to be 147,460 Da. FIG. 3 details the purification process of molecule A with feed material from a 2000 L bioreactor grown for 14 days. The material was centrifuged using a disc stack centrifuge using optimized settings for product recovery and clarification. In campaign 2 the centrate (or supernatant) was then depth filtered with Pall PDE2 and PDD1 filters (or equivalent) followed by sterile filtration. This was followed by the capture step using Protein A (MabSelect SuRe LX, GE Healthcare), and the subsequent purification steps: anion exchange (AEX using Capto Q, GE Healthcare), cation exchange (CEX using Capto SP ImpRes), viral reduction filtration (VRF), and formulation. In campaign 3 the activated carbon filter was implemented inline between depth filtration and the sterilizing filter (0.2 μm pore diameter).

The capture chromatography purification step reduces levels of host cell impurities and cell culture medium components which do not bind to the resin. The product is bound to the column at neutral pH. Bound product is eluted from the column using 30 mM sodium acetate, pH 3.7.

Figure 2:
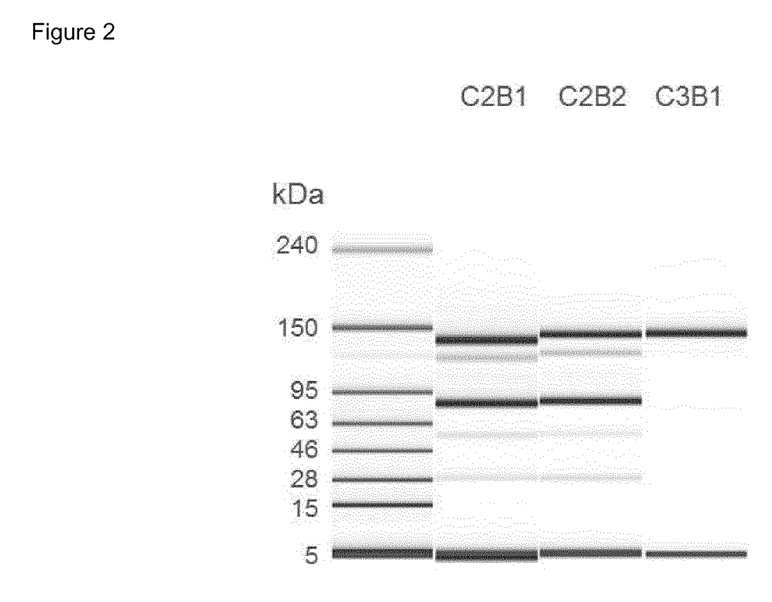
FIG. 2: Non-reducing bioanalyser of Protein A eluate samples of Molecule A. The samples are Protein A eluate samples from manufacturing campaign 2 batch 1 and batch 2 (C2B1 and C2B2 respectively), without use of a carbon filter, and campaign 3 batch 1 (C3B1) in which the carbon filter was implemented. The halfmer seen in the batch 2 samples is not seen in the batch 3 sample.

Antibody reduction was detected in the capture eluate samples analysed by non-reducing bioanalyzer, see FIG. 2. The analytical method is used to determine the purity of samples and the presence of impurities generated by antibody reduction in non-reducing conditions by means of an on-Chip-Electrophoresis assay. The assay consists of two major steps: Covalent binding of protein with a fluorescent dye (labeling), and separation and detection of labeled proteins with on-Chip-Electrophoresis.

The on-Chip assay consists of an interconnected set of gel-polymer filled micro-channels that sieve proteins by size as they are driven through it by means of electrophoresis. The equipment used is a 2100 Bioanalyzer with 2100 Expert software (supplied by Agilent, reference #G2940CA), and a high sensitivity protein analysis kit (supplied by Agilent technologies, reference #5067-1575.).

The samples are Protein A eluate samples from manufacturing campaign 2 batch 1 and batch 2 (C2B1 and C2B2 respectively), in which a carbon filter was not implemented during the primary recovery, and campaign 3 batch 1 (C3B1)

in which the carbon filter was implemented. The antibody reduction products (halfmer and free chains) seen in the campaign 2 samples are not seen in the campaign 3 sample.

Figure 6:
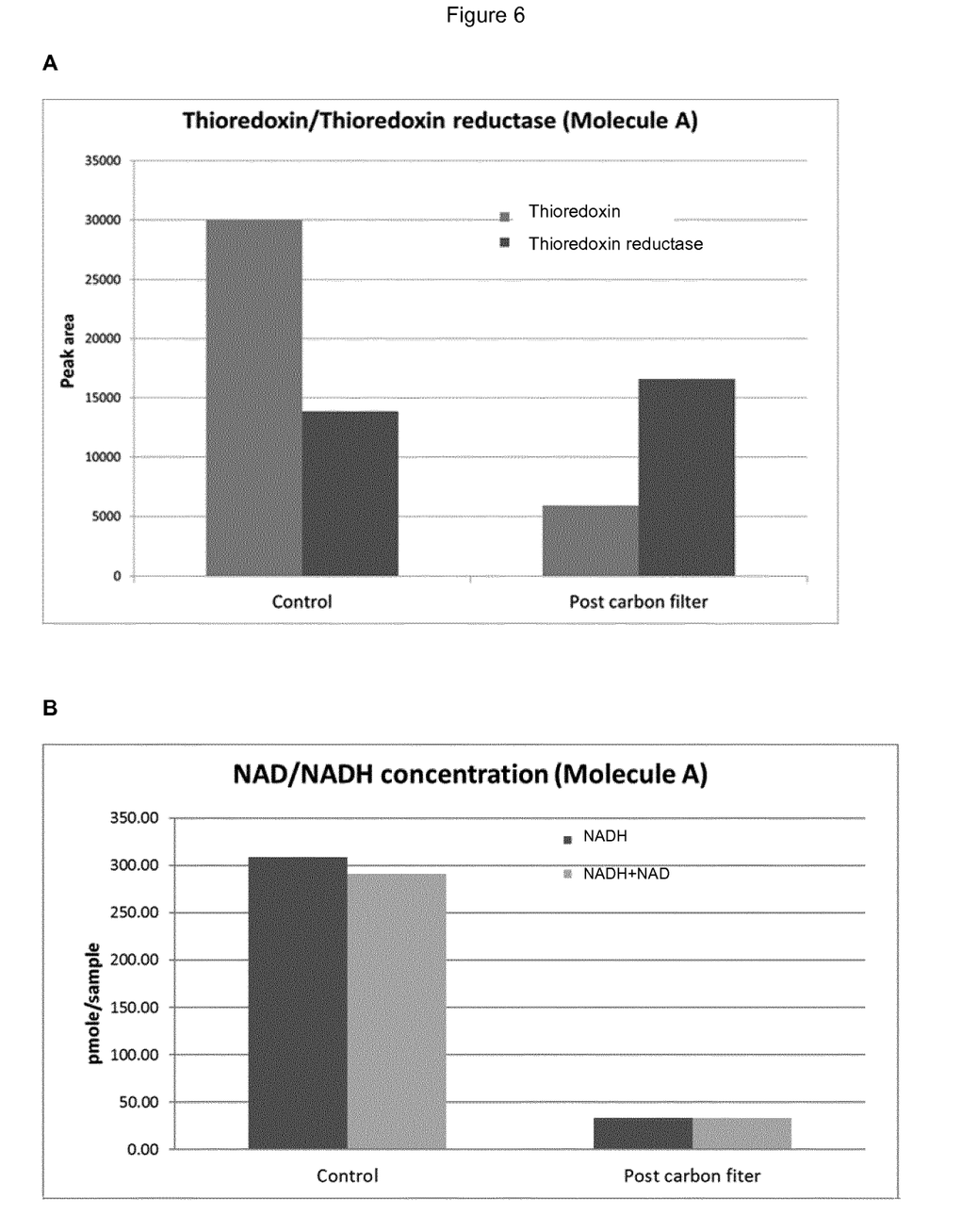
FIG. 6: Molecule A Clarified cell culture fluid (CCCF) with depth and sterile filtration (Control), and after introduction of a carbon filter between the depth and sterile filters, assayed for the reducing agents thioredoxin (A), NAD/NADH (B), and NADP/NADPH (C).

FIG. 6 shows samples of Clarified cell culture fluid (CCCF) for Molecule A, with depth and sterile filtration (Campaign 2 process, Control), and after introduction of a carbon filter between the depth and sterile filters (Campaign 3 process), assayed for the reducing agents thioredoxin, NAD/NADH, and NADP/NADPH. Lower levels of these reducing agents are detected following introduction of the carbon filter. Thioredoxin reductase is however not removed by carbon filtration.

Nicotinamide adenine dinucleotide (NAD) is an enzymatic cofactor involved in many redox reactions. NAD functions as an electron carrier, cycling between the oxidized (NAD) and reduced (NADH) forms. The Sigma Aldrich NAD/NADH Quantification Kit MAK037 detects NAD and NADH, and their ratio without prior purification from the sample. This assay is specific for NAD and NADH, and does not detect NADP or NADPH. NADtotal (NAD and NADH) or NADH are quantified in a colorimetric assay (450 nm).

Nicotinamide adenine dinucleotide phosphate (NADP) is an enzymatic cofactor involved in many redox reactions where it cycles between the reduced (NADPH) and oxidized (NADP) forms.

The Sigma Aldrich NADP/NADPH Quantification Kit MAK038 detects NADP and NADPH, and their ratio, without prior purification from the sample. This assay is specific for NADP and NADPH, and does not detect NAD or NADH. NADPtotal (NADP and NADPH) or NADPH are quantified in a colorimetric assay (450 nm).

Thioredoxin and Thioredoxin reductase are measured using the Simon Simple Western assay. Samples are treated with SDS/DTT and heat denatured. Samples are then loaded into capillaries, separated by size and immobilized to the capillary wall via a proprietary UV capture method. Target proteins are immunoprobed with an antibody (anti thioredoxin pathway/anti glutaredoxin) followed by HRP-amplified chemiluminescent detection (rabbit anti goat HRP conjugate).

The decreased level of impurities in campaign 3 compared to campaign 2 resulted in higher step yields on the subsequent cation exchange chromatography step, designed to remove low molecular weight species and high molecular weight species. The shelf life of material from campaign 3 was also longer than material from campaign 2.

Example 2: Prevention of Antibody Reduction in a 400 L Bioreactor Scale Process In the present example the manufacture of Molecule B at 400 L scale exhibited significant antibody reduction in campaign 1 batch 1 after the protein A capture chromatography step. In the subsequent manufacturing batches an activated carbon filtration step (Millistak+CR40, Millipore) was implemented in the primary recovery process as depicted in FIG. 3. No antibody reduction was detected in these batches.

Molecule B is a humanized monoclonal IgG4P antibody. It is expressed in a CHO DG44 cell line in a fed batch bioreactor process and purified with a 3-step chromatography process. The theoretical intact mass for the complete glycosylated IgG molecule was determined to be 146,372 Da (to the nearest whole Dalton).

Figure 4:
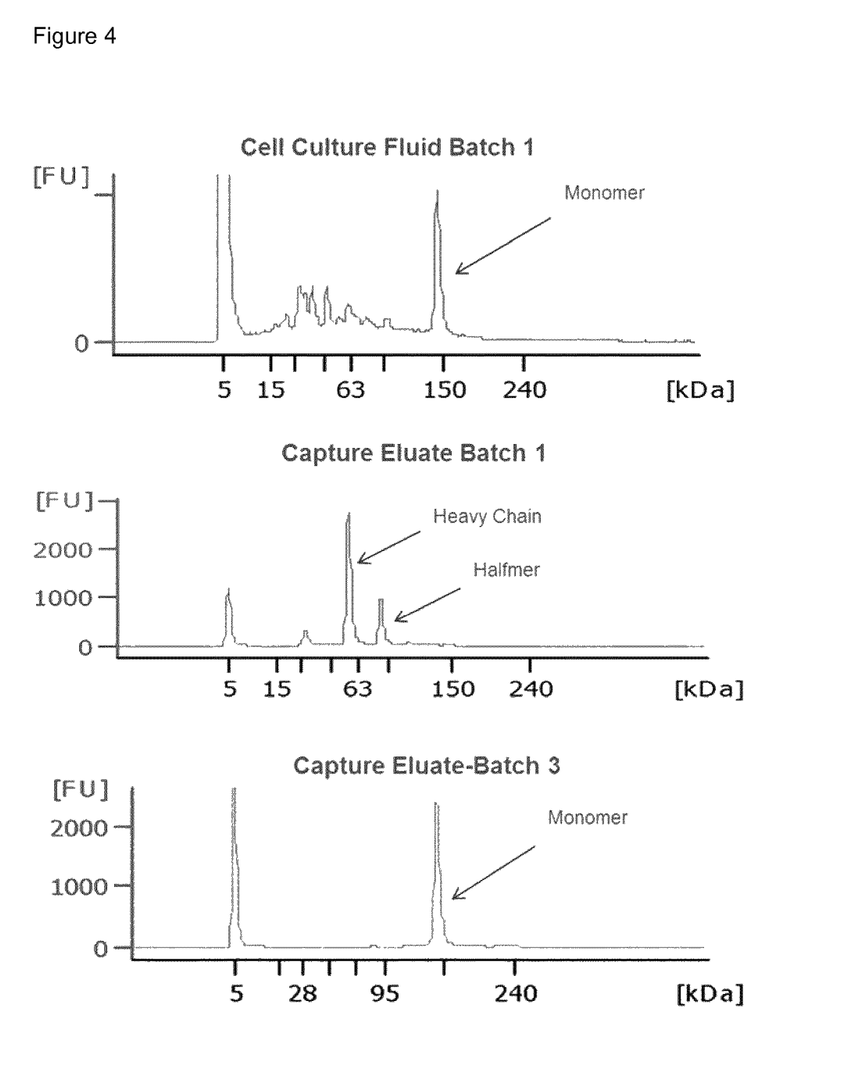
FIG. 4: Non-reducing bioanalyser of IgG Molecule B manufacturing samples. The samples shown are clarified cell culture fluid and capture eluate (after Protein A chromatography) for batch 1, in which the antibody was reduced forming halfmer and free heavy chain. The capture eluate for batch 3 is also shown, in which the activated carbon filter had been implemented in the primary recovery and the antibody molecule was still monomeric after the Protein A capture step.

The purification process was very similar to that of molecule A in example 1. A difference was the elution buffer from the protein A chromatography column being 100 mM sodium acetate, pH3.7. A non-reducing bioanalyzer of IgG Molecule B manufacturing samples shown in FIG. 4, shows clarified cell culture fluid and capture eluate samples (after Protein A chromatography) for batch 1, in which the monomer reduced forming halfmer and heavy chain. The capture eluate sample for batch 3 is also shown, in which the activated carbon filter had been implemented in the primary recovery and the molecule was still monomeric after the Protein A capture step.

Figure 7:
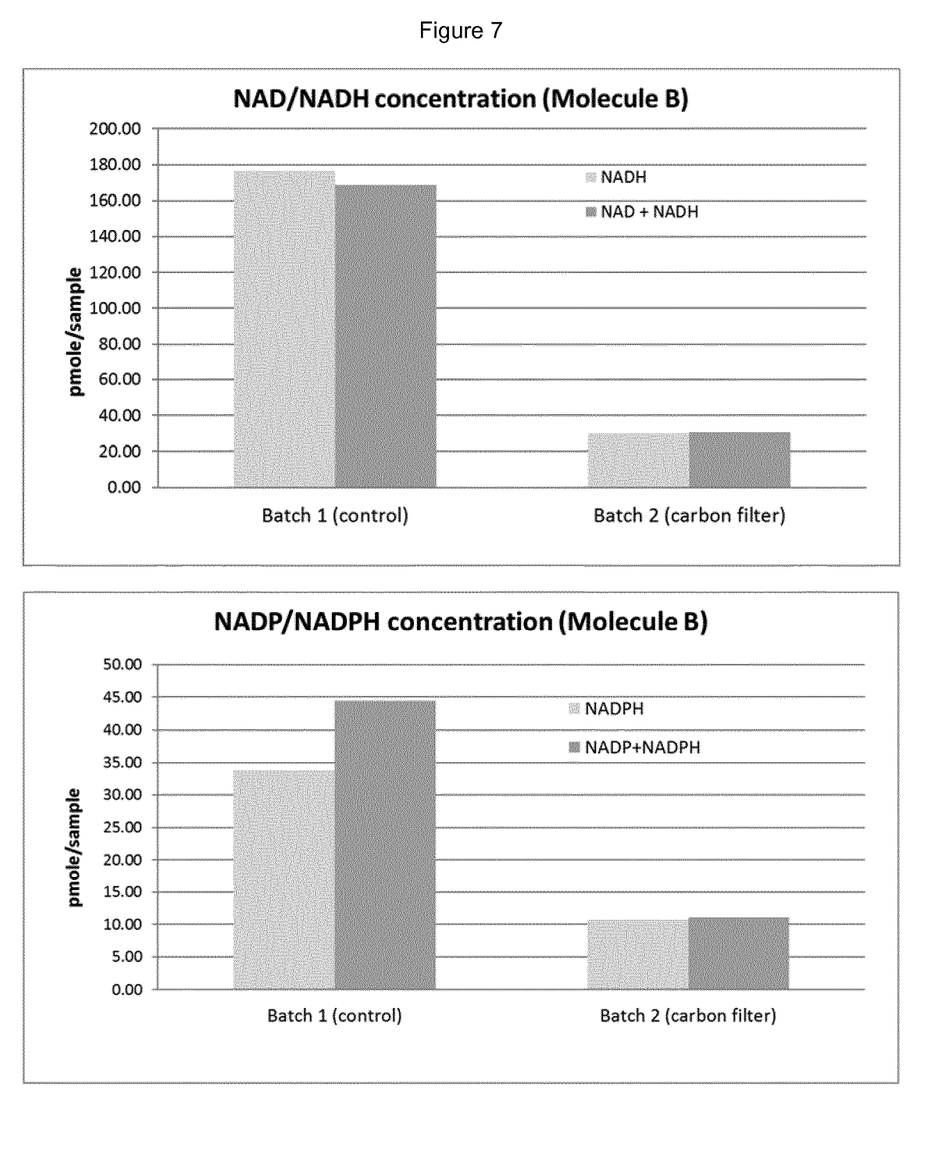
FIG. 7: Molecule B Clarified cell culture fluid (CCCF) from Batch 1 (before introduction of a carbon filter, control) and Batch 2 (after carbon filter implementation), assayed for the reducing agents NAD/NADH, and NADP/NADPH.

FIG. 7 shows Clarified cell culture fluid (CCCF) for Molecule B from Batch 1 (before introduction of a carbon filter, Control) and Batch 2 (after carbon filter implementation), assayed for the reducing agents NAD/NADH, and NADP/NADPH. Lower levels of these reducing agents are detected following introduction of the carbon filter.

Example 3

Samples were taken from the manufacturing campaign of Molecule B after filtration (with and without carbon filtration) but were then purified under low oxygen conditions, using a scale down model of the manufacturing process. This model involved sparging the samples with Nitrogen gas for at least 30 minutes which were then stored in these conditions overnight.

Figure 5:
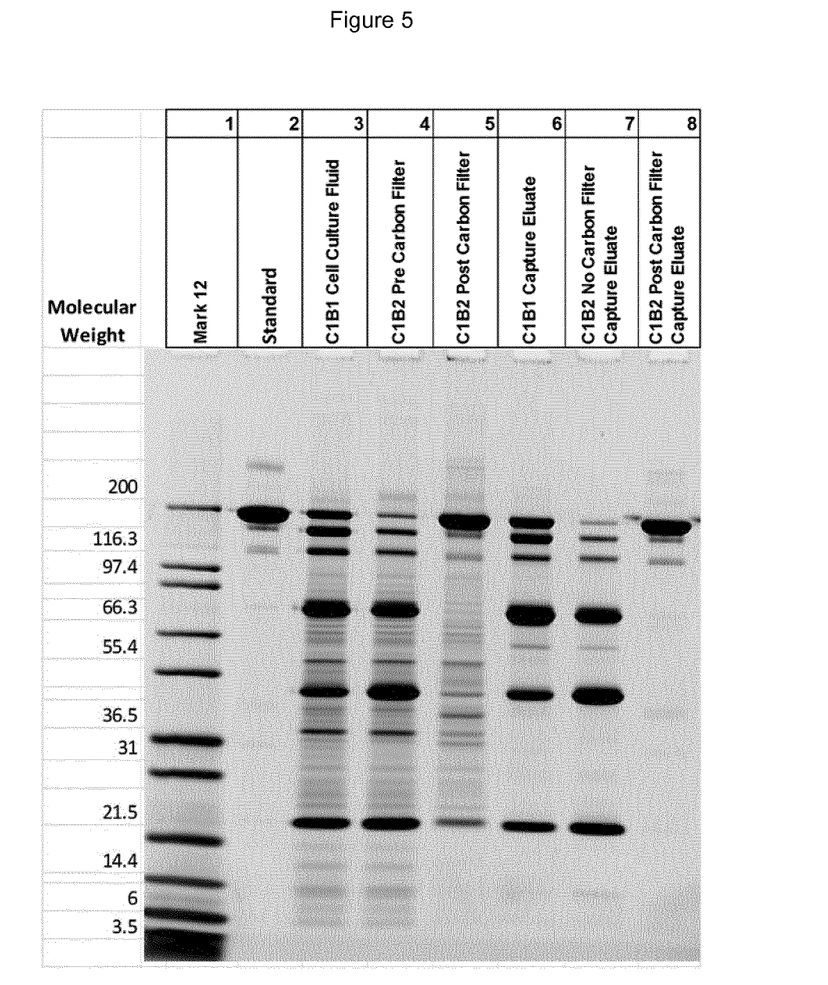
FIG. 5: Sypro stained non-reducing SDS-PAGE analysis of Manufacturing samples of Molecule B. Lane 1: Molecular Weight Standard, Lane 2: Molecule 1 reference standard, Lane 3: Campaign 1 batch 1 cell culture fluid, Lane 4: Campaign 1 batch 2 pre-carbon filter, Lane 5: Campaign 1 batch 2 post carbon filter, Lane 6: Campaign 1 batch 1 capture eluate, Lane 7: Campaign 1 batch 2 no carbon filter capture eluate, Lane 8: Campaign 1 batch 2 post carbon filter capture eluate.

The results of this process as analysed using Sypro stained non-reducing SDS-PAGE may be seen on FIG. 5. This analytical method is used to determine the purity of samples and the presence of impurities generated by Antibody reduction in non-reducing conditions. The gels used were NuPAGE 4-20% Tris-Glycine 10×15 wells 1.5 mm from Thermo Fisher (Cat #EC6028). A Mark 12 Molecular Weight Standard is shown (Thermo Fisher, #L05677). The gel was run at a constant voltage of 125V. The staining was performed using SYPRO ruby red fluorescent stain (Bio-Rad, cat #170-3125).

The samples pre capture step, lanes 3, 4, and 5, were then frozen (≤−60° C.) and defrosted just before analysis. The samples in lanes 6, 7, and 8, were purified by Protein A in a bag sparged with Nitrogen gas, and the eluate samples were then frozen and defrosted just before analysis.

The campaign 1 batch 1 cell culture fluid and capture eluate samples contain low levels of monomer and high levels of the impurities resulting from antibody reduction. The campaign 1 batch 2 sample taken before the carbon filter and the capture eluate from this sample both contained high levels of impurities related to antibody reduction. The sample taken after the carbon filter and the capture eluate from this sample contained high levels of monomer and low/no levels of the impurities resulting from antibody reduction. Therefore the carbon filtration is inhibiting the formation of reduced antibody products observed after protein A chromatography.

The invention claimed is:

1. A method for manufacturing an antibody or fragment thereof comprising:
   expressing said antibody or fragment thereof in a host cell;
   recovering a mixture containing the antibody or fragment thereof, host cell debris, and impurities; and
   purifying said antibody or fragment thereof from the mixture wherein said purification comprises:
   activated carbon filtration, followed by
   protein A chromatography.

2. The method according to claim 1, wherein said purification comprises at least one further chromatography step.

3. The method according to claim 2, wherein said further chromatography steps comprise cation exchange chromatography and/or anion exchange chromatography.

4. The method according to claim 1, wherein the recovered antibody or fragment thereof comprises native disulfide bonds.

5. The method according to claim 1, wherein the recovered antibody or fragment thereof comprises native inter-chain disulfide bonds.

6. The method according to claim 1, wherein said host cell is a mammalian host cell and the mixture containing the antibody is the cell culture supernatant.

7. The method according to claim 6, wherein said purification process additionally comprises depth filtration of the cell culture supernatant prior to activated carbon filtration.

8. The method according to claim 2, wherein depth filtration and activated carbon filtration are operated in-line.

9. The method according to claim 1, wherein the antibody or fragment recovered from the protein A chromatography comprises less than 10%, less than 5%, less than 4%, less than 3%, less than 2% or less than 1% antibody reduction related impurities.

10. The method according to claim 1, wherein the antibody or fragment recovered from the protein A chromatography comprises less antibody reduction related impurities than the antibody or fragment recovered from the same process without an activated carbon filtration step.

11. A method for the prevention of disulfide bond reduction during purification of an antibody or fragment thereof expressed in a host cell comprising:
activated carbon filtration step, followed by
protein A chromatography.

12. A method for purifying an antibody or fragment thereof from a liquid mixture containing contaminants comprising:
filtering said liquid mixture with an activated carbon filter, followed by
protein A chromatography.

13. The method according to claim 12, wherein said recovered antibody or fragment thereof comprises native disulfide bonds.

14. The method according to claim 13, wherein the recovered protein comprises native inter-chain disulfide bonds.

15. A method for decreasing the amount of reducing agents during purification of an antibody or antibody fragment thereof comprising:
activated carbon filtration, followed by
protein A chromatography.

* * * * *